United States Patent
Hollander

(10) Patent No.: US 7,081,225 B1
(45) Date of Patent: Jul. 25, 2006

(54) METHODS AND APPARATUS FOR DISINFECTING AND STERILIZING FLUID USING ULTRAVIOLET RADIATION

(76) Inventor: Brad C. Hollander, P.O. Box 1270, Minden, NV (US) 89423

( * ) Notice: Subject to any disclaimer, the term of this patent is extended or adjusted under 35 U.S.C. 154(b) by 354 days.

(21) Appl. No.: 09/619,520

(22) Filed: Jul. 19, 2000

Related U.S. Application Data

(60) Provisional application No. 60/144,638, filed on Jul. 20, 1999.

(51) Int. Cl.
    *C02F 1/32* (2006.01)
(52) U.S. Cl. .................. 422/24; 250/436; 210/748; 313/489; 313/635; 313/636
(58) Field of Classification Search ............... 313/489, 313/635, 636; 422/24, 121; 210/748; 250/435, 250/436
    See application file for complete search history.

(56) References Cited

U.S. PATENT DOCUMENTS

| | | | |
|---|---|---|---|
| 2,382,939 A | 8/1945 | Koch | 240/11.4 |
| 3,179,792 A | 4/1965 | Weiss | 240/11.4 |
| 3,563,241 A | 2/1971 | Evans | |
| 3,640,391 A * | 2/1972 | Carpenter, Jr. | 210/169 |
| 3,899,392 A | 8/1975 | Grossman et al. | 176/68 |
| 3,936,246 A | 2/1976 | Beitzel | |
| 3,979,633 A | 9/1976 | Davis et al. | 313/481 |
| 3,996,474 A | 12/1976 | Lowther | |
| 4,048,537 A | 9/1977 | Blaisdell et al. | 313/489 |
| 4,071,335 A | 1/1978 | Barosi | 55/68 |
| 4,077,899 A | 3/1978 | van Gils | 252/181.4 |
| 4,100,415 A | 7/1978 | Blaisdell et al. | |
| 4,112,485 A | 9/1978 | Sutter | 362/369 |
| 4,127,361 A | 11/1978 | Hellier et al. | 417/48 |
| 4,141,830 A | 2/1979 | Last | 210/63 Z |
| 4,306,887 A | 12/1981 | Barosi et al. | 55/68 |
| 4,342,662 A | 8/1982 | Kimura et al. | 252/181.4 |
| 4,762,613 A | 8/1988 | Snowball | |
| 4,804,886 A | 2/1989 | Nolan | 313/489 |
| 4,963,750 A | 10/1990 | Wilson | 250/436 |
| 4,968,489 A | 11/1990 | Peterson | 422/186.3 |
| 5,006,244 A | 4/1991 | Maarschalkerweerd | 210/243 |
| 5,043,626 A | 8/1991 | Nolan | 313/489 |
| 5,106,495 A | 4/1992 | Hughes | 210/139 |
| 5,118,988 A | 6/1992 | della Porta | 313/561 |

(Continued)

FOREIGN PATENT DOCUMENTS

JP          03165893 A  *  7/1991

(Continued)

OTHER PUBLICATIONS

Block, Seymour S. Disinfection, Sterilization, and Preservation, 4th ed., 1991, p. 555.*

(Continued)

*Primary Examiner*—E. Leigh McKane

(57) ABSTRACT

An apparatus for sterilizing or disinfecting fluids, which comprises a fluid conduit, an ultraviolet light source, which is at least partially within the fluid conduit, and an air drive unit coupled to the fluid conduit. The ultraviolet light source generates an ultraviolet light, which kills microorganisms in the fluid, thus sterilizing or disinfecting the fluid. The air dive unit creates air bubbles in the fluid, such as for fish tanks, fish hatchery ponds, or the like. In accordance with one embodiment of the present invention, the ultraviolet light source comprises an ultraviolet light bulb being surrounded by a protective sleeve. The protective sleeve preferably comprises a UV transmissive material, which may comprise a fluoropolymer material, such as PTFE, FEP, PFA, AF and Tefzel ETFE.

25 Claims, 8 Drawing Sheets

U.S. PATENT DOCUMENTS

| | | | |
|---|---|---|---|
| 5,200,156 A | 4/1993 | Wedekamp | 422/186.3 |
| 5,320,749 A | 6/1994 | Mullen | |
| 5,322,569 A | 6/1994 | Titus et al. | |
| 5,334,347 A | 8/1994 | Hollander | 422/24 |
| 5,372,781 A | 12/1994 | Hallett et al. | |
| 5,441,179 A | 8/1995 | Marsh | 222/190 |
| 5,451,790 A | 9/1995 | Enge | 250/436 |
| 5,451,791 A | 9/1995 | Mark | 250/438 |
| 5,471,063 A | 11/1995 | Hayes et al. | 250/436 |
| 5,493,124 A | 2/1996 | Shapiro | 250/373 |
| 5,503,800 A | 4/1996 | Free | 422/24 |
| 5,532,549 A | 7/1996 | Duzyk et al. | 313/489 |
| 5,587,069 A | 12/1996 | Downey, Jr. | |
| 5,614,151 A | 3/1997 | LeVay et al. | 422/24 |
| 5,635,059 A | 6/1997 | Johnson | |
| 5,690,057 A | 11/1997 | Curry | |
| 5,729,085 A | 3/1998 | Sica et al. | |
| 5,753,996 A | 5/1998 | Csoknyai | 313/318.05 |
| 5,780,860 A | 7/1998 | Gadgil et al. | |
| 5,792,433 A | 8/1998 | Kadoya | |
| 5,817,276 A | 10/1998 | Fencl et al. | 422/24 |
| 5,937,266 A | 8/1999 | Kadoya | |
| 6,007,781 A | 12/1999 | Campbell et al. | |
| 6,020,402 A | 2/2000 | Anand et al. | |
| 6,038,120 A | 3/2000 | May et al. | |
| 6,042,720 A | 3/2000 | Reber et al. | 210/85 |
| 6,066,919 A * | 5/2000 | Bowser et al. | 313/636 |
| 6,090,281 A | 7/2000 | Buckner | |
| 6,117,335 A | 9/2000 | Bender | |
| 6,221,247 B1 | 4/2001 | Nemser et al. | |
| 6,245,183 B1 | 6/2001 | Iorio | |
| 6,614,039 B1 | 9/2003 | Hollander | |

FOREIGN PATENT DOCUMENTS

| | | | |
|---|---|---|---|
| JP | 07039273 A * | 2/1995 | |
| JP | 07236884 A * | 9/1995 | |
| JP | 10286301 A * | 10/1998 | |
| WO | WO99/58453 | 11/1999 | |

OTHER PUBLICATIONS

Light Sources, Inc. Product Innovations for the '90's; *Germipak™ UV Cells Integral Germicidal Lamps and Sleeves*, p. 25.

* cited by examiner

METHODS AND APPARATUS FOR DISINFECTING AND STERILIZING FLUID USING ULTRAVIOLET RADIATION

CROSS-REFERENCES TO RELATED APPLICATION

This patent application claims the benefit of U.S. Provisional Patent Application Ser. No. 60/144,638, filed Jul. 20, 1999, the entirely of which is incorporated herein by reference for all purposes.

BACKGROUND OF THE INVENTION

The present invention relates generally to methods and apparatus for disinfecting and sterilizing fluids using an ultraviolet light source, and more particularly to a novel pump which can be used in a wide variety of harsh environments to pump fluid and kill micro organisms living in the fluids.

The use of ultraviolet light sources for sterilizing and disinfecting fluids is well-known in the art. A typical ultraviolet light source has two primary parts, the tube and the base. The tube usually comprises a soft glass or quartz casing which holds a vaporizable material, such as mercury, and a starting gas and/or stabilizing gas, such as argon, neon, zeon or the like. The tube also includes one or more electrodes, which when provided with power, excite the gas and the vaporizable material. The excited vaporizable material causes a plasma field which generates the ultraviolet light.

In addition to the tube, an ultraviolet light source typically comprises a base, which is designed to hold the tube in place during operation, but which allows the tube to be removed and replaced when necessary.

While ultraviolet light sources have been used for some time for sterilization purposes, a problem with the ultraviolet light sources currently known in the art is that they are fragile and typically cannot handle the harsh environments in which they must be used. For example, because the prior art ultraviolet light sources are made of soft glass or quartz, the lamps tend to break easily. In addition, because of the adhesive nature of the soft glass or quartz casing, residue and other impurities tend to build up on the lamps over time, affecting the performance of the lamp. Finally, the prior art ultraviolet light sources have a tendency to be expensive and difficult to maintain. Therefore, what is needed is an inexpensive, impact resistant ultraviolet light source, which can be used for sterilization purposes, can be easily introduced into existing systems, is thermally stable in cold or hot fluids including air, and does not require significant modification of the system.

SUMMARY OF THE INVENTION

According to the invention, an apparatus for sterilizing or disinfecting fluids, which comprises a fluid conduit, an ultraviolet light source, which is at least partially within the fluid conduit, and an air drive unit coupled to the fluid conduit. The ultraviolet light source generates an ultraviolet light, which kills microorganisms in the fluid, thus sterilizing or disinfecting the fluid. The air dive unit creates air bubbles in the fluid, such as for fish tanks, fish hatchery ponds, or the like. As one skilled in the art will appreciate, the air bubbles also can help speed-up the killing effect of the ultraviolet light, thus making the sterilizing of disinfecting aspect of the apparatus more effective.

In accordance with one embodiment of the present invention, the ultraviolet light source comprises an ultraviolet light bulb being surrounded by a protective sleeve. The protective sleeve preferably comprises a UV transmissive material, which may comprise a fluoropolymer material, such as PTFE, FEP, PFA, AF and Tefzel ETFE.

A more complete understanding of the present invention may be derived by referring to the detailed description of preferred embodiments and claims when considered in connection with the figures, wherein like reference numbers refer to similar items throughout the figures.

DESCRIPTION OF THE SPECIFIC EMBODIMENTS

The present invention relates generally to methods and apparatus for disinfecting and sterilizing fluids and the surfaces of containers, pipes, ducts and other suitable devices with which the fluids contact. More particularly, the present invention relates to a novel embodiment of an ultraviolet light source, which performs the disinfecting and sterilizing processes using a fluid conduit.

In accordance with the present invention, the term fluid means a continuous, amorphous substance whose molecules move freely past one another and that has the tendency to assume the shape of its container; that is, a fluid can be a liquid or gas, including air. In addition, the term may refer to plasma type materials.

Figure 1:
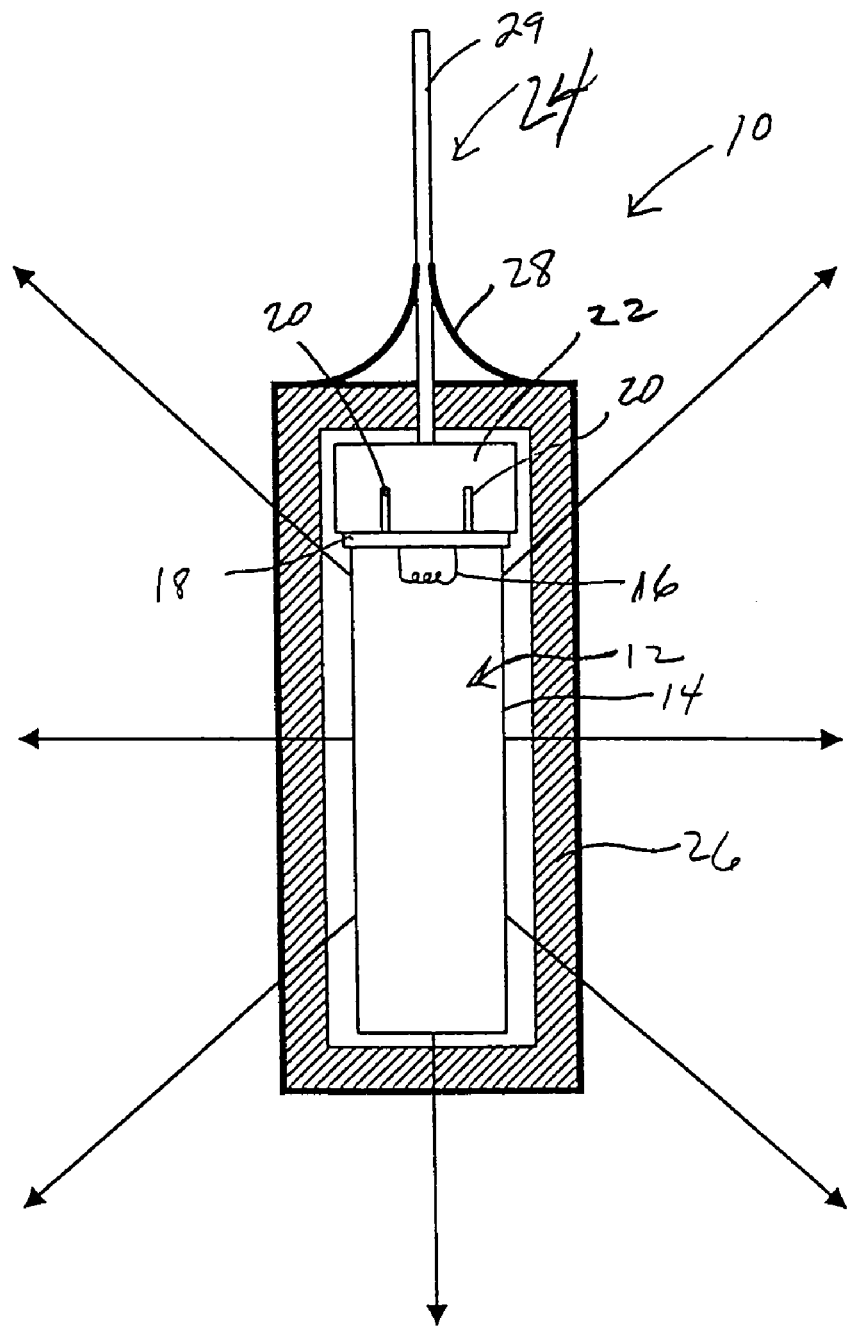
FIG. 1 is a side cross-sectional view of an ultraviolet light source having a protective sleeve.

Referring now to FIG. 1, an apparatus 10 for disinfecting and/or sterilizing a fluid is shown. In accordance with the illustrated embodiment, Apparatus 10 preferably comprises an ultraviolet lamp or light bulb 12, a ballast 22, a power source 24, and a protective coating or sleeve 26.

Ultraviolet lamp 12 preferably comprises a soft glass or quartz tube 14, and at least one filament electrode 16 which preferably is mounted on an end seal 18. One or more base pins 20 are connected to end seal 18, and are adapted to insert into base 22 which, as discussed in more detail below, provides power to ultraviolet lamp 12 through end pins 20.

Glass tube 14 preferably is filled with one or more rare gases, such as argon, neon, xenon and/or krypton. In addition, a small amount of mercury or other suitable metal element is provided within glass tube 14. During operation of ultraviolet lamp 12, electrons are emitted from electrode 16, which is heated when power from base 22 is provided to lamp 12. The electrons are accelerated by the voltage across the tube until they collide with the mercury or other metal atoms, causing them to be ionized and excited. When the mercury or other metal atoms return to their normal state, spectral lines in both the visible and the ultraviolet regions are generated. The low and/or mid pressure within glass tube 14 enhances the ultraviolet radiation.

As one skilled in the art will appreciate, base 22 may include a ballast which is configured to provide a starting voltage and current for lamp 12, and limit the lamp current to the required value for proper operation. In addition, for rapid-start type lamps, the ballast can provide low-voltage cathode heating. The ballast may be a fixed-impedance type ballast, a variable-impedance type ballast or any other suitable electronic ballast currently known in the art. Preferably, electrical source 24 is configured to provide power to base 22 and the bulbs of which may be configured within the base. In addition, while the ballast may be configured within base 22, one skilled in the art will appreciate that the ballast may be separate from base 22, and power is provided from the ballast to base 22 via an electrical lead connection.

In accordance with a further aspect of the present invention, base 22 may comprise a metal, a ceramic material, a plastic material, or a material which allows UV light to pass, such as a fluoropolymer material, or a silicon polymer or silicone material.

Protective coating or sleeve 26 may comprise any suitable UV transmissive material. In accordance with one embodiment, sleeve 26 comprises a fluoropolymer material, which is transparent to ultraviolet light, such as the Teflon® family of products like PTFE, FEP, PFA, AF, Tefzel® ETFE. Alternatively, protective coating of sleeve 26 may comprise a suitable silicon polymer or silicone material, or sleeve 26 may comprise other UV transmissive materials. Protective sleeve 26 protects the soft glass or quartz tube 14 from high impact collisions. As one skilled in the art will appreciate, fluoropolymer and silicone coatings are resistant to impacts, and therefore will protect the glass tube. In addition, in situations in which the soft glass or quartz casing actually breaks from a high impact collision, protective sleeve 26 is adapted so that it contains the glass or quartz particles and harmful mercury material therein, preventing the glass and mercury from getting into the fluid in which the lamp is placed. Moreover, protective sleeve 26 acts as an insulating layer, keeping the temperature of the lamp and in particular the temperature of the plasma within tube 14 at a more stable, proper operating temperature. In accordance with this particular aspect of the present invention, the insulating protective sleeve can be a single sleeve or a double insulating sleeve. In either case, the single or dual layered sleeve acts as a thermal insulator.

Finally, because of the inert nature of the fluoropolymer sleeves as well as other suitable UV transmissive sleeves, apparatus 10 can be placed in many environments that are not suitable for the quartz or soft glass lamps currently known in the art. For example, apparatus 10 having sleeve 26 can be used in medical environments or other industrial environments using caustic chemicals. That is, apparatus 10 can be used to disinfect or sterilize pharmaceutical materials or other materials having low and/or high pH levels, because sleeve 26 does not interact with these materials. Also, because the fluoropolymer materials and some other UV transmissive materials have inherent anti-adhesion properties, apparatus 10 can be placed in many fluids or fluid environments, such as sewage treatment facilities, or the like, without caustic or corrosive materials adhering to the sleeve. As one skilled in the art will appreciate, ultraviolet lamps which merely have a quartz or soft glass tube, often have problems with caustic or corrosive materials adhering to them.

Figure 2:
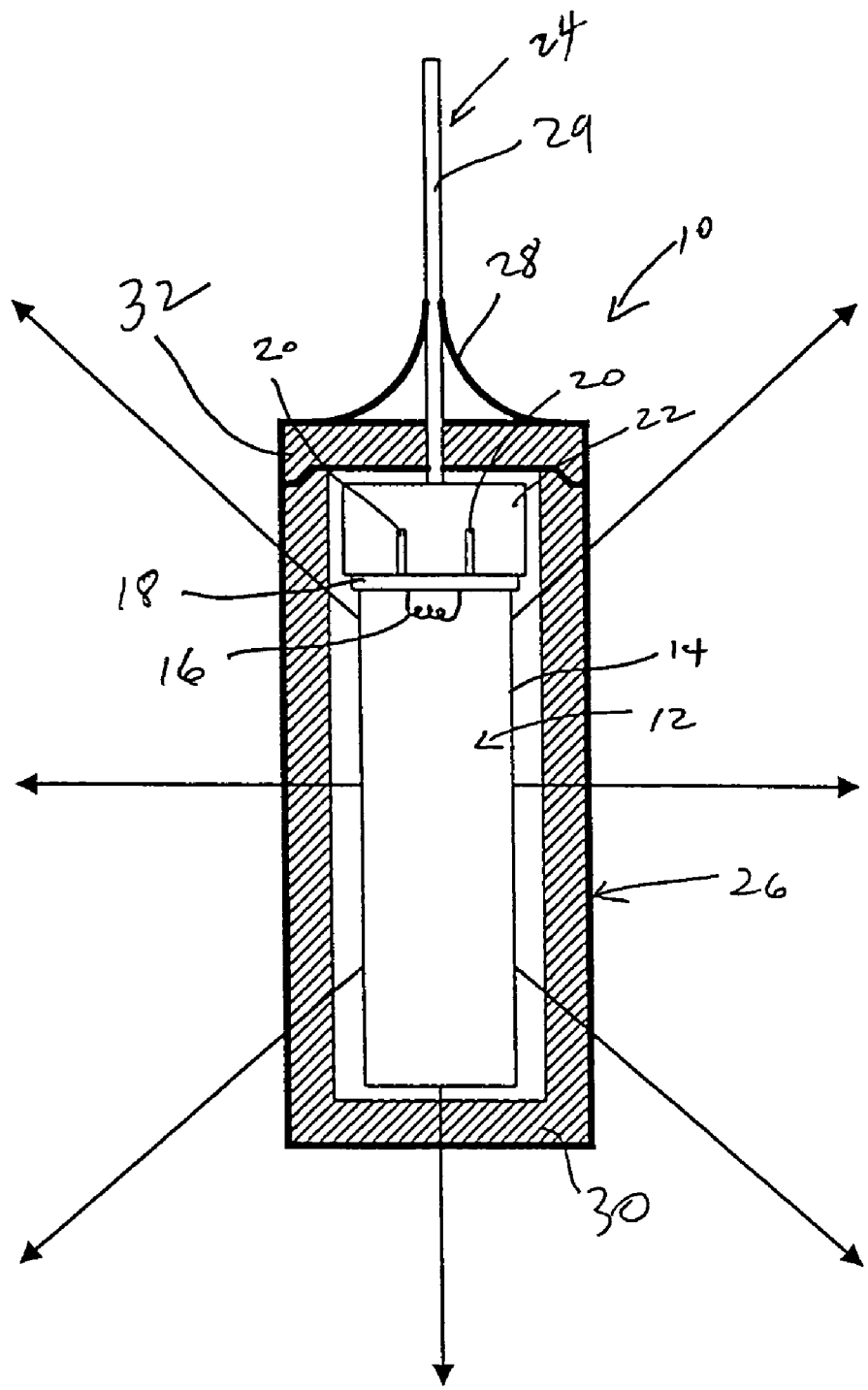
FIG. 2 is a side cross-sectional view of an ultraviolet light source having a protective sleeve with a removable cap.

As illustrated in FIG. 1, protective sleeve 26 may comprise a single piece of coating which surrounds ultraviolet lamp 12 and ballast 22. Coating 26 may be formed around lamp 12 and base 22 by any suitable molding technique known in the art. In addition, as illustrated in FIG. 2, coating 26 may be configured from multiple pieces. For example, as illustrated in FIG. 2, coating 26 preferably comprises a body portion 30 and a cap or lid portion 32. Lid portion 32 may be removably attached to body portion 30 so that one can readily access lamp 12. In accordance with this aspect of the invention, lamp 12 may be changed in the event of its failure or malfunction, or a different lamp 12, for example a lamp emitting different ultraviolet wave lengths, can be used in different fluid types.

Sleeve 26 may be any shape that is suitable for its intended application. For example, sleeve 26 may be cylindrical, spherical, square, or sleeve 26 may be a particular shape to fit into a specific location or to provide specific fluid dynamic characteristics when apparatus 10 is placed in a fluid containing device. Moreover, as discussed in more detail below, sleeve 26 may be shrink-wrapped or pressed onto ultraviolet lamp 12 and/or base 22, so that sleeve 26 takes on the shape of the lamp and ballast assembly. Alternatively, the ultraviolet lamp can be dipped into a liquid fluoropolymer material or other suitable UV transmissive containment material as discussed above in liquid form. Thus, when the lamp is removed, a film of the fluoropolymer or other material forms on and to the shape of the lamp assembly. As one skilled in the art will appreciate, the lamp assembly can take on any suitable shape or form.

Power source 24 preferably is connected in electrical communication with base 22 and comprises any suitable power source. For example, as illustrated in FIGS. 1 and 2, power source 24 may be an AC or DC power source located a distance from base 22 and lamp 14. In this manner, a suitable electrical connector 29 connects power source 24 with base 22. If power source 24 comprises a long electrical connector, connector 24 may be covered by a suitable insulating layer, or it may be covered by a fluoropolymer, silicone or other UV transmissive material such as that used for sleeve 26. In addition, a seal 28 may be provided around electrical connector 29 for preventing fluids and other materials from seeping through the interface between protective sleeve 26 and electrical connector 29. Seal 28 preferably comprises a flexible material so that it can relieve some of the stress put on electrical connector 29 by the movement of apparatus 10.

In accordance with an alternative embodiment of the present invention, power source 24 may be a battery pack or solar power generator connected directly to base 22. In accordance with this particular embodiment, sleeve 26 preferably covers both light source 12 and power source 24. In addition, if power source 24 comprises a battery pack or solar power generator connected directly to base 22, then base 22 preferably will include the ballast therein.

Figure 3:
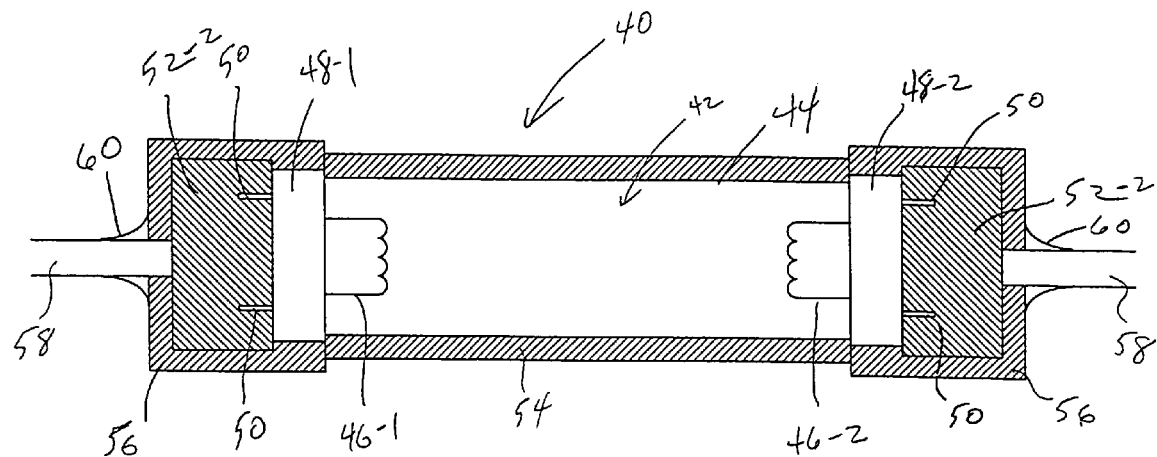
FIG. 3 is a side cross-sectional view of a first embodiment of an ultraviolet light source having a protective sleeve or coating surrounding the light source.

Referring now to FIG. 3, another embodiment of an ultraviolet light source 40 is illustrated. In accordance with this particular embodiment of the present invention, ultraviolet light source 40 preferably comprises an ultraviolet lamp 42 having a quartz or glass tube 44 and two electrodes 46-1 and 46-2 disposed at opposite ends of tube 44. As with the embodiments described above with reference to FIGS. 1 and 2, tube 44 preferably is lined with a phosphor material and it is filled with an inert gas and a metal element. Light source 40 further includes two end seals 48-1 and 48-2 disposed at both ends of tube 44. End seals 48-1 and 48-2 both include base pins 50 which electrically couple lamp 42 to a base 52, having a first end 52-1 and a second end 52-5. In accordance with the embodiment of the present invention illustrated in FIG. 3, tube 44 preferably is surrounded by a protective coating or sleeve 54, such as a fluoropolymer, silicone or other UV transmissive coating as discussed above. In addition, end seals 48 and base 52 preferably are covered by suitable end caps 56. Like protective coating 54, end caps 56 may comprise a fluoropolymer material, or end caps 56 may comprise a silicon polymer or silicone material or other suitable UV transmissive materials which can be used for this intended purpose. In any event, both protective sleeve 54 and end caps 56 preferably are transparent to the ultraviolet radiations emitting from ultraviolet light source 40. Preferably, lead wires 58 are configured to provide power to base 52, and seals 60 may be provided to seal the interface between end caps 56 and lead wires 58. In addition, as discussed above, base 52 may include a ballast, or the ballast may be separated from, but electrically coupled to base 52.

Protective coating 54 may comprise a rigid tube or container, or protective coating 54 may be a flexible fluoropolymer or silicone material which is heat shrunk around tube 44 of lamp 42. In addition, end caps 56 may be removable from lamp 42 and base 52, so that the lamp can be replaced when necessary, or end caps 56 may be securely bonded to protective coating 54, thus creating a fluid tight seal. As mentioned above, if the quartz or glass tube 44 of lamp 42 happens to break, it is preferable to securely contain the broken glass and caustic mercury material away from the fluid in which the lamp is being used. Preferably, a bonding glue or bonding material, such as RTV, or other silicone materials can be used to securely bond end caps 56 to protective coating 54.

Figure 4:
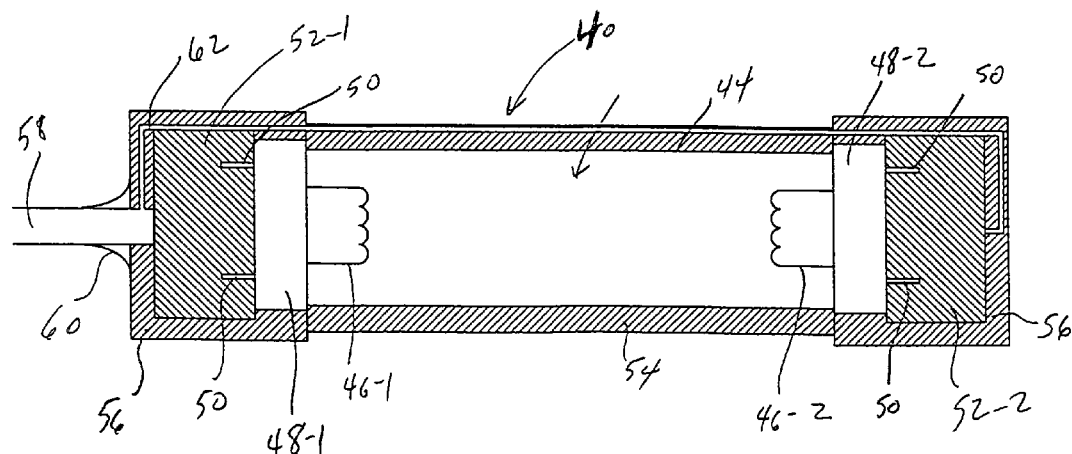
FIG. 4 is a side cross-sectional view of a second embodiment of an ultra light violet light source having a protective sleeve or coating surrounding the light source.

Referring now to FIG. 4, yet another embodiment of an ultraviolet light source 40 is illustrated. This particular embodiment of the present invention is similar to ultraviolet light source 40 of FIG. 3, except only one electrically lead wire 58 is provided. In this manner, a small electrical wire 62 runs from lead wire 58 to second base end 52-2, and provides power to the second base end 52-2.

Figure 5:
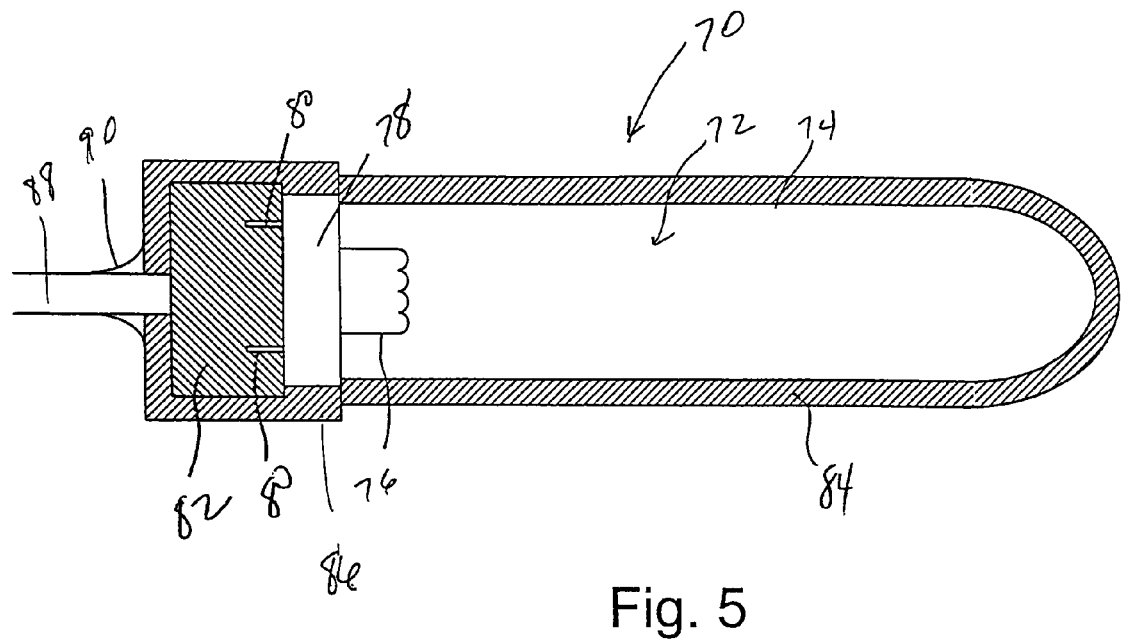
FIG. 5 is a side cross-sectional view of a third embodiment of an ultraviolet light source having a protective sleeve or coating surrounding the light source.

Referring now to FIG. 5, still another embodiment of an ultraviolet light source 70 is shown. In accordance with this particular embodiment of the present invention, ultraviolet light source 70 preferably comprises an ultraviolet lamp 72 having a quartz or glass tube 74 and an electrode 76. As with the other embodiments of the present invention, within glass tube 74 is a metal material, such as mercury, and one or more inert gases, such as argon, neon, xenon or krypton. In addition, at one end of lamp 72 is an end seal 78 having base pins 80, which provide electrical communication to a base 82. Preferably, an electrical lead wire 88 is used to provide power to base 82. As with the embodiments illustrated in FIGS. 3 and 4, tube 74 preferably is surrounded by a protective coating 84 which, as discussed above, preferably comprises a fluoropolymer or silicone material. In addition, an end cap 86 preferably covers base 82 and end seal portion 78 of lamp 72. As with the embodiments discussed above with reference to FIGS. 3 and 4, a seal 90 surrounds electrical lead 88 and prevents fluid from entering between lead 88 and end cap 86. Also, as discussed above, end cap 86 can be removable, or securely bonded to protective coating 84.

Figure 6:
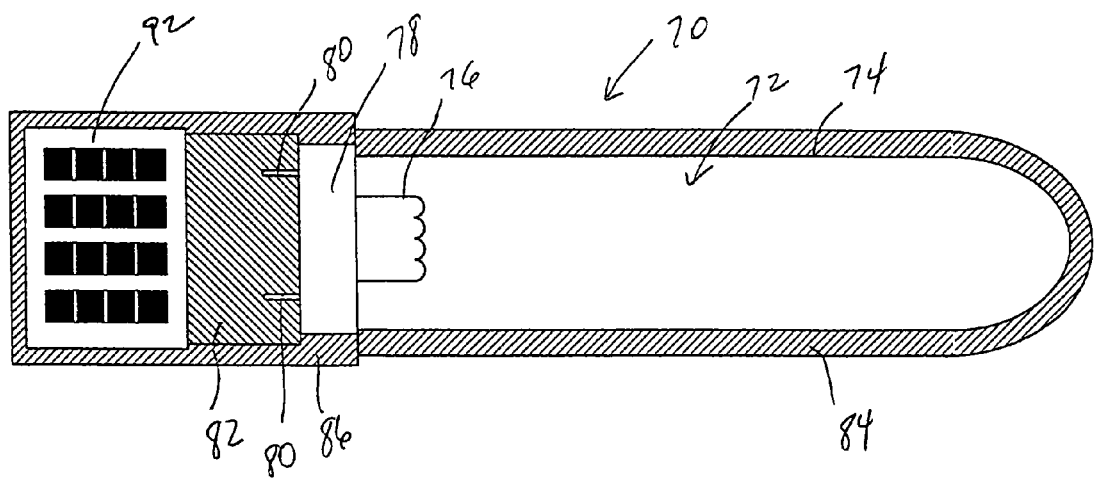
FIG. 6 is a side cross-sectional view of a fourth embodiment of an ultraviolet light source having a protective sleeve or coating surrounding the light source.

Referring now to FIG. 6 another embodiment of ultraviolet light source 70 is illustrated. The embodiment in FIG. 6 is similar to the embodiment of FIG. 5 except that instead of an electrical lead 88 providing power to base 82, a solar power generator 92 provides the power. In accordance with this particular embodiment of the present invention, end cap 86 preferably is configured to cover end seal 78, base 82, and solar power generator 92. In addition, while the embodiment illustrated in FIG. 6 shows a solar power source providing power to ballast 82, a battery pack or other suitable power source can be used in a similar manner.

Figure 7:
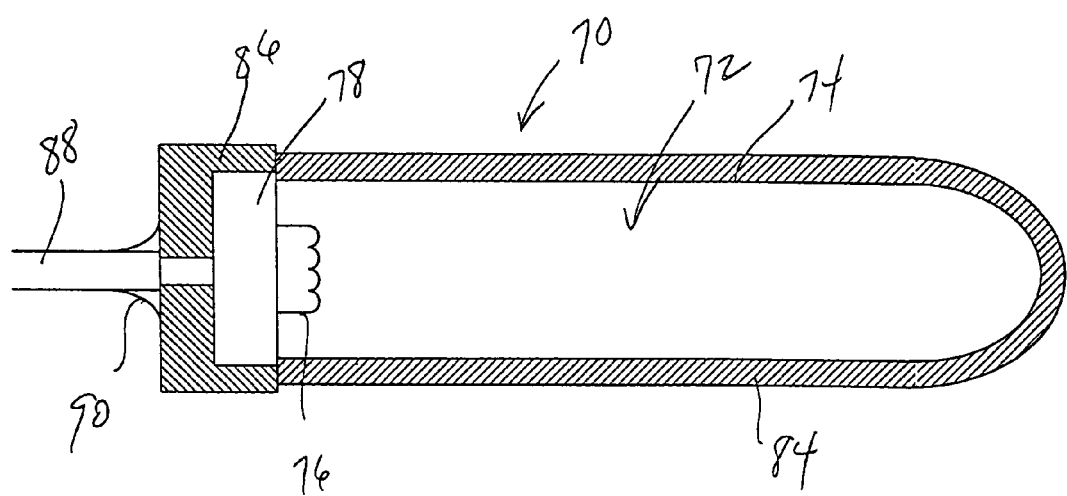
FIG. 7 is a side cross-sectional view of a fifth embodiment of an ultraviolet light source having a protective sleeve or coating surrounding the light source.

Referring now to FIG. 7, yet another embodiment of ultraviolet light source 70 is shown. In accordance with this particular embodiment of the present invention, ultraviolet light source 70 preferably comprises an ultraviolet lamp 72 having a glass or quartz tube 74, an electrode 76, and an end seal 78. In addition, a protective coating 84 is formed around tube 74 and an end cap 86 covers end seal 78 and a portion of electrical lead 88. However, instead of ultraviolet lamp 72 having pins which plug directly into a base, power is provided directly to ultraviolet lamp 72 via electrical lead 88. In accordance with this particular aspect of the invention, the ballast portion of the ultraviolet light source (not shown) is separate from the ultraviolet light source 70. In addition, while the embodiment of FIG. 7 is shown as having a protective coating 84 and an end cap 86, one skilled in the art will appreciate that the two-piece design enables one to change lamp 72 easily. Thus, in accordance with an alternative embodiment, one solid protective coating may be used to cover lamp 72, and end seal 78. Therefore, the present invention is not limited to the illustrated embodiment.

Figure 8:
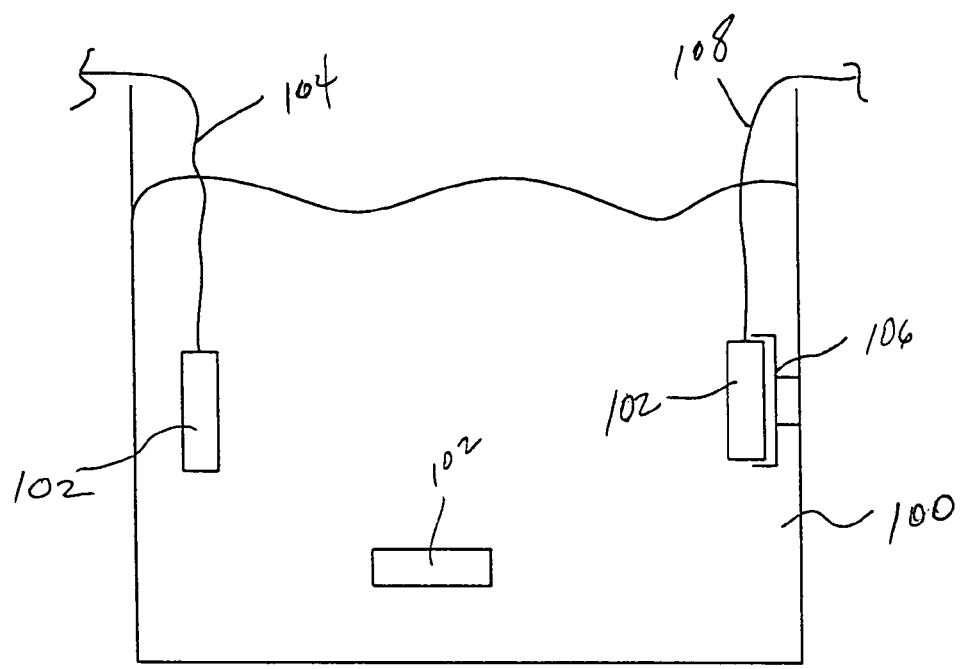
FIG. 8 is a side view drawing of a tank having a plurality of ultraviolet light sources mounted or deposited therein.

The ultraviolet light source of the present invention can be used for disinfecting and sterilizing fluids and fluid containers and handling equipment in a wide variety of different environments. The size and the configuration of the ultraviolet light source can be modified for use in various water or fluid tanks, as well as in air purification systems and handling equipment for fluids, including air and other gases. For example, as illustrated in FIG. 8, one of a variety of ultraviolet light source devices can be placed in a tank with water or other suitable fluid to help kill any organisms which might live within the tank. As illustrated in FIG. 8, an ultraviolet light source 102 may hang within tank 100 by a support line 104. In accordance with one embodiment of the present invention, support line 104 may be a lead wire or tether wire holding light source 102 in a preferred location. Alternatively, support line 104 also may act as an electrical lead line, providing electrical power to ultraviolet light source 102 via that means. Otherwise, in accordance with an alternative embodiment of the present invention, a battery pack, a solar power generator or other suitable power providing means may be used to provide power to light source 102. Similarly, an ultraviolet light source 102 may be secured in tank 100 by a clip 106 or other suitable securing device, and an electrical lead line 108 or a battery pack or the like, may be used. Finally, if ultraviolet light source 102 is powered by a battery pack or solar powered generator, the ultraviolet light source may be dropped into tank 100 without any supporting lines. In this manner ultraviolet light source 102 may drift to the bottom of tank 100, or it may be configured to float within the fluid tank.

Figure 9:
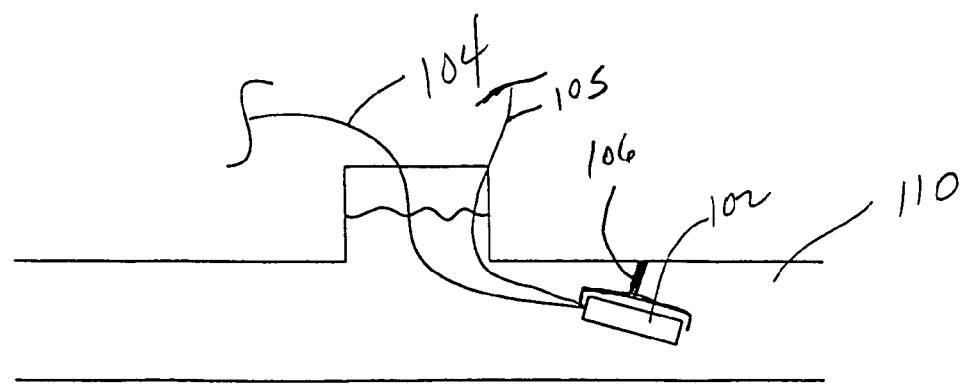
FIG. 9 is a side view drawing of a fluid carrying pipe having an ultraviolet light source deposited therein.

Referring now to FIG. 9, an alternative use of an ultraviolet light source 102 is illustrated. In this particular embodiment of the present invention, ultraviolet light source 102 is placed within a fluid pipe 110 which is configured to carry any number of different fluid types. Preferably, ultraviolet light source 102 is suspended within fluid pipe 110 using a support line 104. As with the embodiments illustrated in FIG. 8, support line 104 also may include an electrical lead connector for providing power to ultraviolet light source 102. In accordance with an alternative embodiment of the invention, light source 102 may include an electrical lead connector 104, as well as a separate lead wire 105. In this particular embodiment, the lead wire can be used to hold light source 102 in place, taking the pressure off electrical lead connector 104. Also, lead wire 105 can be used to move the light source 102 within the pipe 110. Finally, in accordance with yet another embodiment of the present invention, light source 102 may be mounted within fluid pipe 110 with, for example, a mounting bracket or clip 106.

Figure 10:
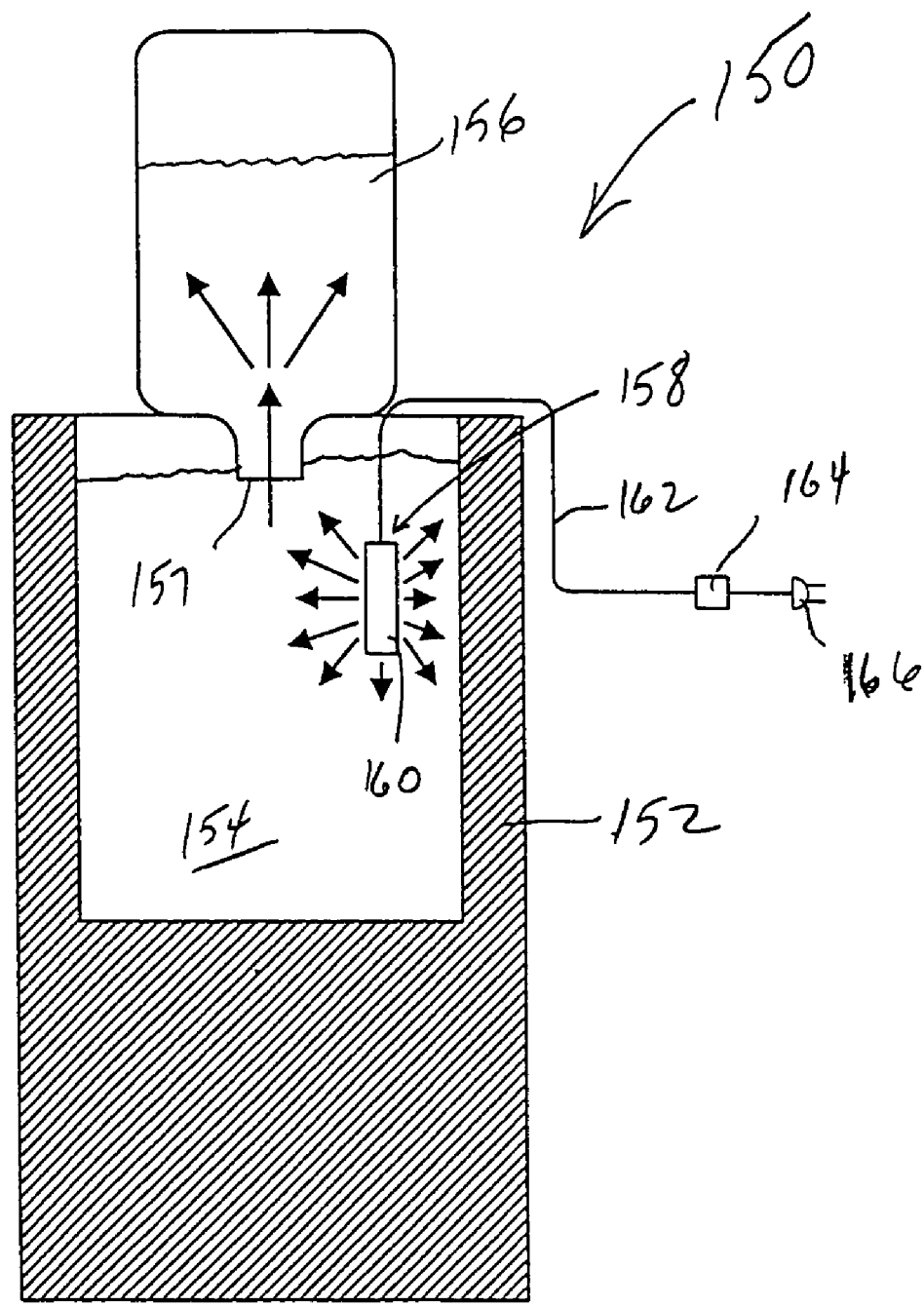
FIG. 10 is a side cross-sectional view of a water dispenser having an ultraviolet light source therein.

Referring now to FIG. 10, a use of an ultraviolet source in a drinking water dispenser 150 is shown. In accordance with this particular embodiment of the present invention, drinking water dispenser 150 preferably includes a base 152 having a water reservoir 154 therein, and a water bottle 156 provided in an inverted position on top of base 152 directly above reservoir 154. As one skilled in the art will appreciate, as water in reservoir 154 lowers below opening 157 in water bottle 156, water from water bottle 156 will pour into reservoir 154. In this manner, the water level in reservoir 154 is maintained.

In accordance with this particular embodiment of the present invention, an ultraviolet light source 158 preferably is placed in reservoir 154 of drinking water dispenser 150. Ultraviolet light source 158 preferably includes a light bulb 160, an electrical connector 162 for providing power to the light source. In addition, in accordance with the illustrated embodiment, light source 158 also may include an external ballast 164, and an AC plug adapter 166. When ultraviolet light source 158 is turned on, the UVC light emitted from the light source kills all the microorganisms that may be living in the water within reservoir 154 or on the sides of reservoir 154. In addition, the ultraviolet light source also may pass through opening 157 in water bottle 156, killing any microorganisms that may be living in water bottle 156. In this manner, the ultraviolet light 158 can be used to sterilize reservoir 154, the water within reservoir 154, water bottle 156, and the water within water bottle 156. Thus, the ultraviolet light source can be used as a safe and effective means to maintain a clean water environment. In addition, as mentioned above, because ultraviolet light source 158 and, in particular light bulb 160 of light source 158 preferably is enclosed in a protective coating, a corrosive film from algae and other organisms will not form on light bulb 160. In addition, if by chance light bulb 160 happens to break, the protective coating surrounding light bulb 160 will contain the broken glass and other materials from the light bulb, preventing those materials from being exposed to the water. In this manner, the water within reservoir 154 and water tank 156 will not be exposed to any harmful materials from lamp 160.

Figure 11:
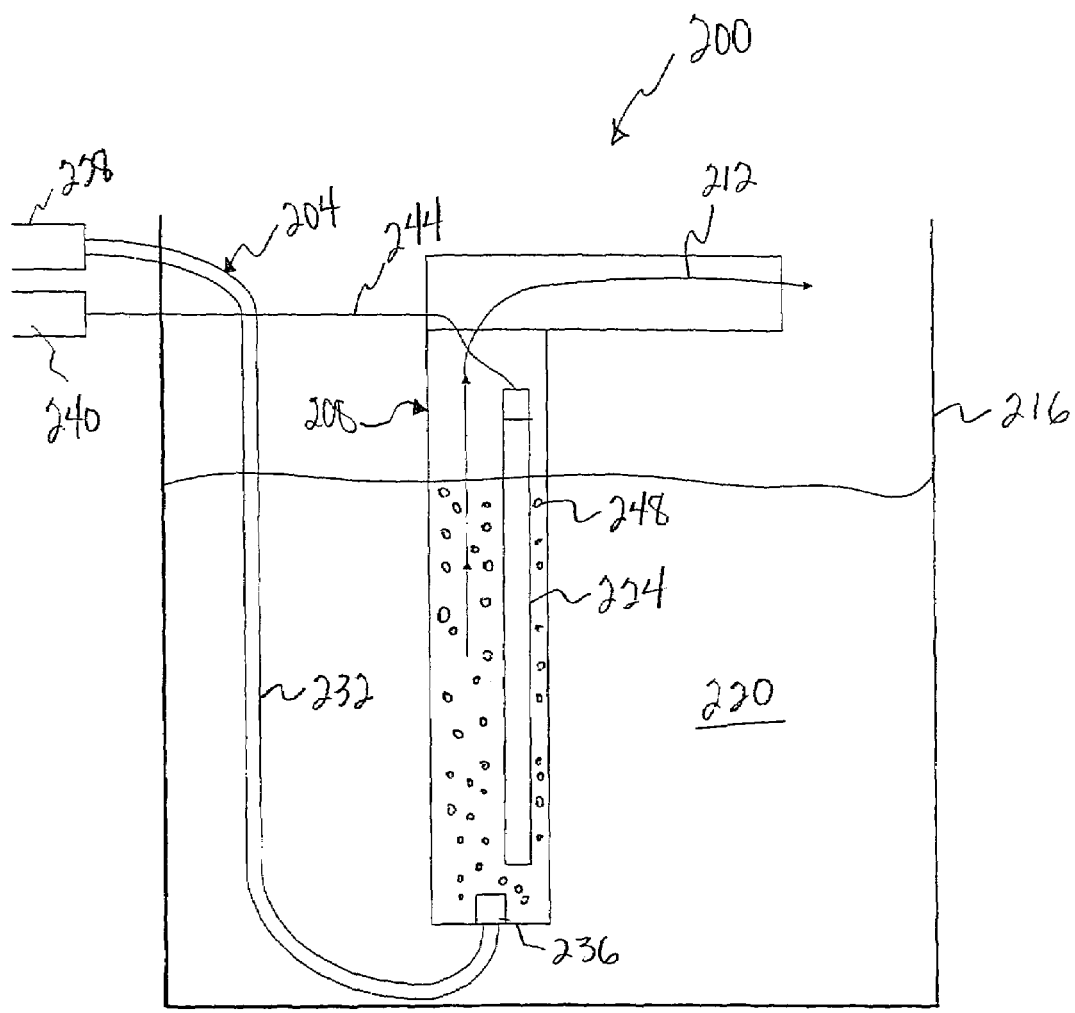
FIG. 11 is a side cross-sectional view of a fluid pump with an ultraviolet light source therein.

With reference to FIG. 11, a fluid pump and purification system 200 is shown. To purify liquid 220 in a tank 216, the system includes a fluid conduit 208, an air drive unit 204 and an ultraviolet source 224. The air drive unit 204 produces bubbles 248 in the fluid conduit 208 to promote water flow in the direction indicated by the arrow 212. Additionally, heat produced by the ultraviolet source 224 promotes water flow by convection.

The air drive unit 204 provides pumping force to the liquid in the conduit 208. Additionally, the air bubbles 248 promote disinfection and sterilization. The air drive unit 204 includes an air pump 228, an air hose and a aerator 236. Gas is forced down the air hose 232 and out the aerator 236 by the air pump 228. To promote bubble formation 248, the aerator is porous like a filter. Other embodiments could pump air through the fluid conduit 208 using the same principles discussed above for the pumping of liquid.

The light source 224 provides ultraviolet light to the fluid conduit 208. To additionally sterilize outside of the conduit 208, it may be translucent to ultraviolet light. An low voltage ballast 204 provides excitation energy to the light source 224 through an electrical conduit 244. As discussed in relation to the previous figures, the light source 224 may include a plastic coating over a glass enclosure or the enclosure itself may be plastic without any glass. The heated enclosure of the light source 224 can produce ozone in addition to any ozone provided from the air drive unit 204. Different materials used for the enclosure can produce differing amounts of ozone.

Although not shown in the figure, the fluid conduit 208 is secured to the tank for support. The method for attachment preferably allows easily removing the conduit 208 and replacing the light source 224. The fluid conduit 208 is attached to a liquid sealing cover, panel or plate which attaches to the tank 216.

The fluid 220 in the tank 216 is disinfected and sterilized in this system 200 by the combination of the air drive 204 and ultraviolet light 224. As described above, the air drive unit 204 places small bubbles 248 of gas in the fluid conduit 208. The presence of bubbles 248 increases the germicidal effect of the ultraviolet light source 224. These air bubbles 248 mix and agitate the fluid to better expose the contaminants to ultraviolet light. Preferably, this gas is ozone which also oxidizes the contaminants to further sterilize and disinfect.

The flow through the liquid conduit 208 is adjustable according to need. For example, a large tank 216 may require higher flow through the conduit 208. By adjusting the air produced by the air pump 228 and the heat produced by the light source 224, the flow through the liquid conduit 208 is adjustable. Some embodiments may include a fluid flow sensor or other sensor to provide feedback to enhance control of the flow.

This system 200 is useful in many different applications for disinfecting and sterilizing of liquids or gasses. These applications include cooling towers, air conditioner coils, drain pans, sumps, hydraulic heating systems, portable and industrial humidifiers, air ducts, floor sinks, condensation pipes, fish tanks, swamp coolers, water tanks and troughs, food refrigeration units, dishwashers, washing machines, clothes drying machines, pools, spas, ponds, inline conduits or transport pipes, in line pressure tanks, greenhouses, hydroponics, pet water dishes, air compressors, ship ballast, liquid pharmaceuticals, sterilization containers, dispensing equipment, oxygen tanks, scuba air supply systems, water purification, or fluoroscopy. Further, the principles discussed herein could be effective in duct installation, underground construction, mining applications, fuel storage, waste product processing, selective kill systems, well water purification, making sun tea, mushroom farming, fish hatcheries, space air and water purification, animal habitats, explosive environments, or identification of iridescent organisms. Further still, the system could disinfect and sterilize metal working fluid, tanks, pipes, and recirculation systems in machine shops; sewage in treatment plants or sewage in single hold configurations; food packages before they contain food; upper air irradiation in hazardous areas; air in food handling areas; pasteurization of water, milk or other consumables before or after sealing the container; food grade liquid processing and storage such as wine making; activation titanium dioxide and other photo reactive compounds; pretreatment for filtration and RO antislim control on filter cartridges; germ warfare tents, anterooms, triage areas, canteens, or other military applications; blood irrigation, dialysis, ambulances, emergency room kits, medical sterilization tanks and boxes, or other medical applications; dental air and water systems; meat or vegetable market displays or misters for vegetable displays; air handling systems such as air curtains and air hoods used in such places as lab applications; or, any closed loop liquid or air handling system. Additionally, the system could be installed in spa covers, the holds of ships, bait tanks, recreation vehicle fluid storage tanks, boat storage tanks, or other applications.

While only a few uses of ultraviolet light source 102 are illustrated in the drawings and disclosed herein, one skilled in the art will appreciate that an ultraviolet light source of the present invention may be used in any environment in which it is desirable to kill micro-organisms such as bacteria, molds, viruses, etc. For example, ultraviolet light source 102 can be used in conjunction with air conditioning devices and other air purification systems to kill the bacteria and molds that live within the air. Similarly, ultraviolet light source 102 can be used in a wide range of water tanks such as bottled water dispensers, RV and boat water tanks, cruise ships, livestock water tanks, and any other suitable fluid environment. In addition, by configuring an ultraviolet light source 102 into a small, compact package, the ultraviolet source can be placed in a glass of drinking water or a pitcher of drinking water to kill any organisms that are living within that immediate glass or pitcher. In this particular embodiment, the ultraviolet light source preferably is a self-contained, battery powered light source.

In conclusion, the present invention provides methods and apparatus for disinfecting and/or sterilizing fluids in a variety of fluid environments. While a detailed description of presently preferred embodiments of the invention have been given above, various alternatives, modifications, and equivalents will be apparent to those skilled in the art. For example, while various ultraviolet lamp configurations are disclosed herein, any number of different lamp configurations may be used without varying from the spirit of the invention. In addition, while various protective sleeves and coatings are disclosed, any shape and configuration of a protective sleeve or coating may be used. Therefore, the above description should not be taken as limiting the scope of the invention which is defined by the appended claims.

The invention claimed is:

1. An apparatus for pumping and sterilizing or disinfecting liquid held in a reservoir, comprising:
    a fluid conduit, which is at least partially submerged in the liquid held in the reservoir;
    an ultraviolet lamp which is at least partially within the fluid conduit, the ultraviolet lamp comprising:
        a tube holding and in direct contact with a gas and a vaporizable metal, the tube comprising a body portion, at least one end portion, and optionally at least one end cap covering said at least one end portion;
        at least one electrode positioned within the tube and electrically coupled to a power source, the at least one electrode operable to excite the gas and the vaporizable metal and thereby generate ultraviolet light; and
        an ultraviolet-transmissive protective coating comprising a fluoropolymer, a silicon polymer, or a silicone material surrounding and in touching proximity with at least the body portion of the tube; and
    an air drive unit coupled to the fluid conduit and adapted to cause a liquid to flow through the fluid conduit and past the portion of the ultraviolet lamp in the fluid conduit, wherein the ultraviolet lamp generates an ultraviolet light which kills microorganisms in the liquid and said fluid conduit, and
    wherein the ultraviolet lamp is disposed within the fluid conduit such that when in use, the protective coating is in direct contact with the liquid within the fluid conduit.

2. The apparatus as recited in claim 1, wherein the protective coating surrounds and is in touching proximity with the body portion and at least a portion of the at least one end portion.

3. The apparatus as recited in claim 1, wherein the protective coating is a fluoropolymer coating.

4. The apparatus as recited in claim 1, wherein the body portion is formed of a fluoropolymer material.

5. The apparatus as recited in claim 4, wherein said fluoropolymer coating is selected from the group consisting of PTFE, FEP, PFA, AF, and ETFE.

6. The apparatus as recited in claim 1, wherein the body portion comprises a quartz or glass material.

7. The apparatus as recited in claim 1, wherein the protective coating comprises a silicon polymer or silicone material.

8. The apparatus as recited in claim 1, wherein the protective coating is selected from the group consisting of a shrink wrapped coating, a form pressed coating, a sprayed coating, and a dipped coating.

9. The apparatus as recited in claim 1, wherein the power source is a solar power source connected to the ultraviolet lamp, and wherein the protective coating surrounds the solar power source and the ultraviolet lamp and seals the solar power source with the ultraviolet lamp.

10. The apparatus as recited in claim 1, wherein the protective coating forms a seal around the tube.

11. The apparatus as recited in claim 1, wherein the at least one end cap comprises a fluoropolymer end cap.

12. The apparatus as recited in claim 1, wherein the at least one end cap comprises a silicone end cap.

13. The apparatus as recited in claim 1, wherein a silicone sealer seals the at least one end cap to the protective coating.

14. A method of pumping and sterilizing or disinfecting a liquid held in a reservoir, comprising the steps of:
    positioning a fluid conduit at least partially submerged in the liquid held in the reservoir;
    placing an ultraviolet lamp at least partially within the fluid conduit, the ultraviolet lamp comprising:
        a tube holding and in direct contact with a gas and a vaporizable metal, the tube comprising a body portion, at least one end portion, and optionally at least one end cap covering said at least one end portion;
        at least one electrode positioned within the tube and electrically coupled to a power source, the at least one electrode operable to excite the gas and the vaporizable metal, thereby generating ultraviolet light; and an ultraviolet-transmissive protective coating comprising a fluoropolymer, a silicon polymer, or a silicone material surrounding and in touching proximity with at least the body portion of the tube;

pumping air into the fluid conduit to pump liquid through the fluid conduit and past at least a portion of the ultraviolet lamp; such that the liquid within the fluid conduit is in direct contact with the protective coating; and illuminating the ultraviolet lamp by exciting the gas and vaporizable metal within the tube so that the ultraviolet light is generated, killing microorganisms in the liquid and the fluid conduit.

15. The method as recited in claim 14, wherein the protective coating is a fluoropolymer coating.

16. The method as recited in claim 15, wherein said fluoropolymer coating is selected from the group consisting of PTFE, FEP, PFA, AF, and ETFE.

17. The method as recited in claim 14, wherein the body portion is formed of a fluoropolymer material.

18. The method as recited in claim 14, wherein the body portion comprises a quartz or glass material.

19. The method as recited in claim 14, wherein the protective coating comprises a silicon polymer or silicone material.

20. The method as recited in claim 14, wherein the protective coating is applied to at least the body portion of the casing by a process selected from the group consisting of heat shrinking the protective coating onto at least the body portion of the tube, form pressing the protective coating onto at least the body portion of the tube, spraying the protective coating onto at least the body portion of the tube, and dipping at least the body portion of the tube into a liquid material.

21. The method as recited in claim 14, wherein the power source is a solar power source connected to the ultraviolet lamp, and wherein the protective coating surrounds the solar power source and the ultraviolet lamp and seals the solar power source with the ultraviolet lamp.

22. The method as recited in claim 14, wherein the protective coating forms a seal around the tube.

23. The method as recited in claim 14, wherein the at least one end cap comprises a fluoropolymer end cap.

24. The method as recited in claim 14, wherein the at least one end cap comprises a silicone end cap.

25. The method as recited in claim 14, wherein the at least one end cap is sealed to the protective coating using a silicone sealer.

* * * * *